United States Patent [19]

Cook et al.

[11] Patent Number: 4,826,823
[45] Date of Patent: May 2, 1989

[54] METHODS OF USING 2-CHLORO-2'-DEOXYADENOSINE-5'-PHOSPHATE AND ITS SALTS

[75] Inventors: Phillip D. Cook, Ann Arbor, Mich.; Roland K. Robins, Irvine, Calif.; Dennis J. McNamara, Ann Arbor, Mich.

[73] Assignee: Warner-Lambert Company, Morris Plains, N.J.

[21] Appl. No.: 812,564

[22] Filed: Dec. 31, 1985

Related U.S. Application Data

[63] Continuation-in-part of Ser. No. 699,391, Feb. 5, 1985, abandoned.

[51] Int. Cl.⁴ ............................................. A61K 31/52
[52] U.S. Cl. ........................................ 514/46; 514/47; 536/26; 536/27; 536/28; 536/29
[58] Field of Search ...................... 536/26, 27; 514/46, 514/47

[56] References Cited

U.S. PATENT DOCUMENTS

| | | | |
|---|---|---|---|
| 3,201,389 | 8/1965 | Fujimoto et al. | 536/27 |
| 3,321,463 | 5/1967 | Moffatt | 536/27 |
| 3,337,529 | 8/1967 | Laufer | 536/27 |
| 3,466,273 | 9/1969 | Sowa et al. | 536/27 |
| 4,167,565 | 9/1979 | Stein et al. | 536/26 |

FOREIGN PATENT DOCUMENTS

| | | | |
|---|---|---|---|
| 190726 | 8/1986 | European Pat. Off. | 514/47 |
| 1358769 | 7/1974 | United Kingdom | 536/27 |

OTHER PUBLICATIONS

Carson et al, I, Proc. Nat. Acap. Sci. USA, vol. 77(11), pp. 6865–6869, 1980.
Carson et al, II, Blood, vol. 62 (4), pp. 737–743, 1983.
Bennett et al, Chem. Abstr., 103:31970r, Aug. 5, 1985.

*Primary Examiner*—Ronald W. Griffin
*Assistant Examiner*—L. Eric Crane
*Attorney, Agent, or Firm*—Krass & Young

[57] ABSTRACT

Nucleotide compounds are provided, namely 2-chloro-2'-deoxyadenosine 5'-phosphate compounds (I) especially as the monosodium and disodium salt, as well as a method for their production, pharmaceutical compositions comprising the compounds, and methods of treatment using the compounds in dosage form. The compounds of the invention have pharmacological properties and are useful antimicrobial agents, antiviral agents, and antileukemic agents.

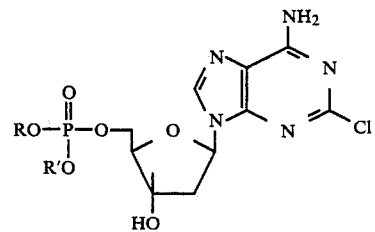

2 Claims, No Drawings

METHODS OF USING 2-CHLORO-2'-DEOXYADENOSINE-5'-PHOSPHATE AND ITS SALTS

CROSS-REFERENCE TO RELATED APPLICATION

This application is a continuation-in-part of application Ser. No. 699,391, filed Feb. 5, 1985, now abandoned.

TECHNICAL FIELD

The invention relates to novel nucleotide compounds, namely 2-chloro-2'-deoxyadenosine 5'-phosphate compounds, to a method for their production, to pharmaceutical compositions comprising the compounds, and to use of the compounds and methods of treatment using the compounds in dosage form. The compounds of the invention have pharmacological properties and are useful antimicrobial agents, antiviral agents, and antileukemic agents.

BACKGROUND OF THE INVENTION

The deoxynucleoside, 2-chloro-2'-deoxyadenosine, is known (D. A. Carson, D. Bruce Wasson, and Ernest Beutler, Proc. Soc. Acad. Sci. USA, Vol. 81 pp. 2232–2236, 1984) for its antileukemic and immunosuppressive activity both in primates and in Phase I clinical trial in patients.

SUMMARY OF THE INVENTION

The invention in one aspect relates to the free acid 2-chloro-2'-deoxyadenosine 5'-phosphate and its basic monosalts and disalts having the structural formula I:

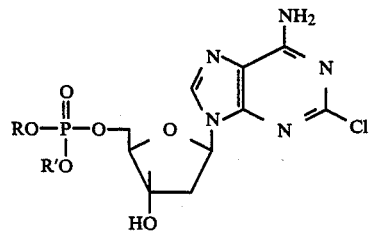

where R and R' of the R-substitution each independently represent H, $NH_4$, an alkali metal, or an alkylamine, or together represent an alkaline earth metal. Preferred compounds are the free acid, 2-chloro-2'-deoxyadenosine 5'-phosphate, and the sodium, potassium, lithium, ammonium, n-butylamine, n-octylamine and triethylamine mono and disalts. Also preferred are the calcium, magnesium and barium monosalts. Whereas the known nucleoside 2-chloro-2'-deoxyadenosine is sparingly soluble in water, the nucleotide compounds as a feature of the present invention differ in solubility ranging from relatively water soluble to relatively water insoluble. Thus the invention allows for a greater latitude both in formulating the proper nucleotide dosage form and in administering the nucleotide over a wider range of dose levels.

The invention in another aspect includes a method for preparing 2-chloro-2'-deoxyadenosine 5'-phosphate compounds having the above formula I, which comprises reacting 2-chloro-2'-deoxyadenosine with a phosphorylating agent and isolating the resulting 2-chloro-2'-deoxyadenosine 5'-phosphate compound in free acid form or salt form. In carrying out the reaction, one uses a suitable medium such as trimethylphosphate and a phosphorylating agent such as phosphoryl chloride. The reaction is carried out in the cold and is usually complete within 3 to 5 hours. For the isolation of the product in a preferred procedure, the reaction mixture is combined with ice water containing sodium bicarbonate sufficient for neutralization. The reaction mixture, after ether extraction, concentration and ethanol precipitation of solids, is further processed as an aqueous filtrate by silica gel column chromatography to obtain a high yield of high purity, chloride-free product. It is found surprisingly that the method is selective for the production of the desired nucleotide phosphate and is substantially free of competing side-reactions such as those involving the unprotected nucleosidic 2-chloro and 3'-hydroxyl of formula I. It is found that the product obtained in the preferred isolation procedure using silica gel chromatography is the monosodium salt. In another preferred isolation procedure for the production of the disodium salt product, one uses column chromatography with a suitable resin preferably with a polysytrene resin having a high porosity rating such as HP20, HP21 or SP207 resin to obtain high purity chloride free product.

In an alternative procedure, the phosphorylation reaction mixture is neutralized in ice water saturated with ammonia, and the resulting ammonium disalt phosphate product is recovered in a manner analogous to the above isolation procedure. In still another procedure, the free acid 2-chloro-2'-deoxyadenosine 5'-phosphate is obtained by subjecting the monosodium salt or disodium salt product to ion exchange with a suitable exchange material in the acid form. To convert the metal ion to a different ion for purposes of isolating the product, ion-exchange chromatography is suitably employed preferably using a given alkali metal salt column, alkaline earth metal salt column or alkylamine salt column respectively of, for example, a sulfonic acid cation-exchanged resin.

In still another preferred procedure, a given mono- or di-salt of the free acid having the structural formula I is obtained by neutralizing the free acid in an aqueous solvent with an equivalent amount of a water soluble salt forming compound and removing the solvent.

The invention in one composition aspect relates to a pharmaceutical composition for treating microbial infection comprising an antimicrobially effective amount of a compound having formula I and a pharmaceutically acceptable carrier.

The invention in another composition aspect relates to a pharmaceutical composition for inhibiting virus growth comprising a virus growth inhibiting amount of a compound having formula I and a pharmaceutically acceptable carrier.

The invention is another composition aspect relates to a pharmaceutical composition for inhibiting the growth of leukemic cells in experimental animals exemplified by rodents such as the mouse, comprising a cell growth inhibiting amount of a compound having the above formula I and a pharmaceutically acceptable carrier.

The invention in another aspect relates to a method for treating microbial infection which comprises administering an antimicrobially effective amount of a compound having formula I to an animal in need thereof.

The invention in another method aspect relates to a method for inhibiting virus growth which comprises administering a virus growth inhibiting amount of a compound having formula I to an animal in need thereof.

The invention in another method aspect relates to a method for inhibiting the growth of leukemic cells which comprises administering a leukemic cell growth inhibiting amount of a compound having formula I to an animal in need thereof.

PHYSICAL AND PHARMACOLOGICAL PROPERTIES OF THE COMPOUNDS

The compounds of the invention are useful as pharmacological agents, as indicated, for the treatment of microbial infection, and viral infection, and for the treatment of leukemia in experimental warm-blooded animals exemplified by rodents such as the mouse. The activity of representative compounds of the invention was established by test protocols described below.

One test protocol is the in vitro antibacterial/antifungal (ABF) test. Compounds are tested for antimicrobial activity in an agar-disk diffusion assay, a standard microbiological technique for testing antibiotics. After incubation of each culture with a test compound, a zone of inhibition is determined. By this test, the present compounds typically are cidal against gram-negative bacterial species (*Escherichia coli* 04863) and gram positive bacteria (*Bacillus subtilis* 04555 and *Streptococcus faecalis* 05045) at concentrations in the range from 500 to 1000 micrograms/ml.

Another test protocol is the in vivo assay for antileukemic activity. This assay is carried out with male $DC_2F_1$ mice (six per treatment group) that weigh 22–24 grams at first treatment. L1210 leukemia cells are harvested from the peritoneal ascites fluid of a leukemic male $DBA_2$ mouse and diluted with sterile 0.9% saline containing 2.1% W/V bovine serum albumin, 2000U/ml penicillin, and 0.3 mg/ml streptomycin. The cells are counted with a Coulter ® counter. The mice are randomized, inoculated with $10^4$ L1210 cells (0.5 ml, i.p.) and rerandomized to treatment or control groups on day zero. The test compound is dissolved in 10% aqueous dimethylsulfoxide. Treatment groups are injected i.p. with 0.5 ml of freshly made DMSO solutions of the test compound once daily on days 3–7. Control mice are treated with 0.5 ml 10% dimethylsulfoxide. All mice are weighed on days 3 and 7 and all dying mice are autopsied to confirm the presence of advanced leukemia. A %T/C value [T/C computed as (median lifespan of the treated group/median lifespan of the control group)] greater than 125 is considered as showing significant activity. The results for nucleotide compounds and compositions of the invention exemplified by 2-chloro-2'-deoxyadenosine 5'-phosphate, sodium salt, are presented in Table I-A.

TABLE 1-A

Antitumor Activity 2-chloro-2'-deoxyadenosine 5'-phosphate Sodium Salt (Example 1a, infra)

| Dose Mg/Kg | Treated Group Survival Time Days | Control Group Survival Time Days | % T/C Animals |
|---|---|---|---|
|  |  | 10.1 |  |
| 50 (33)* | 17.8 |  | 176 |
| 25 (16) | 17.0 |  | 168 |
| 12.5 (8) | 14.8 |  | 146 |
| 6.25 (4) | 12.4 |  | 122 |

*(Dosage expressed on a molar basis).

For comparison, results obtained in the same protocol for the nucleoside 2-chloro-2'-deoxyadenosine are given in the following Table I-B:

TABLE I-B

Antitumor Activity - 2-chloro-2'-deoxyadenosine

| Dose Mg/Kg | Treated Group Survival Time Days | Control Group Survival Time Days | % T/C Animals |
|---|---|---|---|
|  |  | 10.1 |  |
| 50 | 16.8 |  | 166 |
| 25 | 17.0 |  | 168 |
| 12.5 | 16.8 |  | 166 |
| 6.25 | 14.1 |  | 139 |

The results show that the activity of the two compounds at these dose levels is substantially the same. However, although not shown, the nucleotide is protected from degradation by the endogenous enzymes adenosine deaminase and nucleoside phosphorylase so that the nucleotide is in fact superior to the nucleoside.

In one embodiment, 2-chloro-2'-deoxyadenosine 5'-phosphate monosodium salt (also referred to herein as Compound 1) showed inhibiting activity against both small and large viruses of both DNA and RNA types by the virus rating (VR) method of Sidwell et al., Appl. Microbial. 22, 79 (1971). A virus rating that is greater than 1.0 indicates definite antiviral activity. A virus rating of 0.5–0.9 indicates moderate antiviral activity, and a virus rating smaller than 0.5 suggests slight or no apparent antiviral activity. The results of such rating method using Compound 1 compared with results for its parent nucleoside, ribavirin, and selenazofurin, are reported below in Table II. These results were obtained by testing on Microtest II (Falcon Plastics) plastic panels with a monolayer of Vero or HeLa cells.

TABLE II

ANTIVIRAL ACTIVITY OF COMPOUND 1, 2-CHLORO-2'-DEOXYADENOSINE, RIBAVIRIN AND SELENAZOFURIN

Virus Rating

| VIRUS | COMPOUND 1 | 2-chloro-2'-deoxyadenosine | RIBAVIRIN | SELENAZOFUR |
|---|---|---|---|---|
| CMV (AD 169) | 4.1 | 1.95 | 0.7 | 0.6 |
| CMV (TOWNE) | 3.6 | 2.0 | 1.0 | 0.6 |
| ADENO-2 | 0.0 | 0.0 | 1.3 | 1.9 |
| HSV-2 (330) | 0.94 | 0.68 | 0.8 | 1.5 |
| HSV-2 (MS) | 0.54 | 0.38 | 0.8 | 1.5 |
| VV | 1.24 | 0.84 | 1.5 | 2.2 |
| Para-3 | 0.0 | 0.0 | 1.4 | 2.4 |

TABLE II-continued
ANTIVIRAL ACTIVITY OF COMPOUND 1,
2-CHLORO-2'-DEOXYADENOSINE, RIBAVIRIN AND SELENAZOFURIN

| VIRUS | COMPOUND 1 | 2-chloro-2'-deoxyadenosine | RIBAVIRIN | SELENAZOFUR |
|---|---|---|---|---|
| Measles | 0.0 | 0.0 | 1.1 | 1.9 |

The results indicate that 2-chloro-2'-deoxyadenosine 5'-phosphate monosodium salt has good broad spectrum antiviral activity against both DNA and RNA viruses.

PREPARATION OF PHARMACEUTICAL COMPOSITIONS

When used as a pharmacological agent or pharmaceutical composition, the compounds of the composition aspect of the invention can be prepared and administered in any of a wide variety of topical, oral, and parenteral dosage forms.

For preparing pharmaceutical compositions, one uses an inert, pharmaceutically acceptable carrier which carrier can be either solid or liquid. Solid form preparations include powders, tablets, dispersible granules, capsules, cachets, and suppositories. A solid carrier can be one or more substances which may also act as diluents, flavoring agents, solubilizers, lubricants, suspending agents, binders, or tablet disintegrating agents; it can also be an encapsulating material. In powders, the carrier is a finely divided solid which is in admixture with the finely divided active compound. In the tablet the compound is mixed with carrier having the necessary binding properties in suitable proportion and compacted in the shape and size desired. The powders and tablets preferably contain from 5 or 20 to about 70 percent of the active ingredient. Suitable solid carriers are magnesium carbonate, magnesium stearate, talc, sugar, lactose, pectin, dextrin, starch, gelatin, tragacanth, methyl cellulose, sodium carboxymethyl cellulose, a low melting wax, cocoa butter, and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets, and capsules can be used as solid dosage forms suitable for oral administration.

Liquid form preparations include solutions, suspensions, and emulsions. As an example may be mentioned water or water-propylene glycol solutions for parenteral injection. Liquid preparations can also be formulated in solution in aqueous polyethylene glycol solution. Aqueous solutions suitable for oral use can be prepared by dissolving the active component in water and adding suitable colorants, flavors, stabilizing, and thickening agents as desired. Aqueous suspensions suitable for oral use can be made by dispersing the finely divided active component in water with viscous material, e.g., natural or synthetic gums, resins, methyl cellulose, sodium carboxymethyl cellulose, and other suspending agents.

Topical preparations include dusting powders, creams, lotions, gels, and sprays. These various topical preparations may be formulated by well-known procedures. See for example Remington's Pharmaceutical Sciences, Chapter 43, 14th Ed., Mack Publishing Co., Easton, Pa. 18042, USA.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules, and powders in vials or ampoules. The unit dosage form can also be a capsule, cachet, or tablet itself or it can be the appropriate number of any of these packaged forms.

The quantity of active compound in a unit dose of preparation may be varied or adjusted from 50 mg to 500 mg according to the particular application and the potency of the active ingredient.

In therapeutic use as pharmacological agents the compound utilized in the pharmaceutical method of this invention is administered at the initial dosage of about 0.1 mg to about 50 mg per kilogram. A dose range of about 0.5 mg to about 10 mg per kilogram is preferred. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The compound may also be administered parenterally or intraperitoneally. Solutions of the compound can be prepared in water mixed if desired with a surfactant such as hydroxypropylcellulose. Dispersions can also be prepared in glycerol, liquid polyethylene glycols, and mixtures thereof and in oils. Under ordinary conditions of storage and use, these preparations contain preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), N,N-dimethylacetamide, suitable mixtures thereof and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by sterilization accomplished by filtering. Generally, dispersions are prepared by incorporating the various sterilized active ingredients into a sterile vehicle which contains the basic dispersion medium and the required other ingredients from those enumerated above. In the case of the sterile powders for the preparation of sterile injectable solutions, the preferred methods of preparation are vacuum drying and the freeze-drying technique which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

The principal active ingredient is compounded for convenient and effective administration in effective amounts with a suitable pharmaceutically acceptable carrier in unit dosage form as hereinbefore disclosed. A unit dosage form can, for example, contain the principal active compound in amounts ranging from about 0.1 to about 500 mg, with from about 0.5 to about 250 mg being preferred. Expressed in proportions, the compound is generally present in from about 0.1 to about 500 mg/ml of carrier. In the case of compositions containing supplementary active ingredients, the dosages are determined by reference to the usual dose and the manner of administration of the said ingredients. The daily parenteral doses ranges from 0.1 mg/kg to 10 mg/kg. The preferred daily dose range is 0.3 mg/kg to 10 mg/kg. The preferred daily dose range is 0.3 mg/kg to 10 mg/kg.

The invention and the best mode for practicing the same are illustrated by the following examples. In the examples temperatures are given in degrees Celsius.

EXAMPLE 1

2-Chloro-2'-deoxyadenosine 5'-phosphate monosodium salt and disodium salt (a) To an ice-cooled solution of 2.85 g (10 mmol) of 2-chloro-2'-deoxyadenosine in 60 ml of trimethylphosphate was added dropwise 1.53 g (10 mmol) of phosphoryl chloride in ten minutes. The solution was stirred for three hours and then an additional 382 mg (2.5 mmol) of phosphoryl chloride was added. The solution was stirred further for an hour and poured into 100 g ice-water containing 8 g (95 mmol) of NaHCO$_3$. This solution was stirred for one hour at ambient temperature and then extracted 2 times with ether. The aqueous layer was evaporated in vacuo to 50 ml and treated with ethanol to precipitate salts which were filtered. This process was repeated to remove additional salts. The filtrate was mixed with 10 g of silica gel and evaporated in vacuo. The powdered residue was slurried in acetonitrile and placed on a column of silica gel (280 g, Kiesel gel 60, 70-230 mesh ASTM) packed in acetonitrile-water (4/1). Elution with acetonitrile-water (4/1) provided a tlc pure, chloride-free fraction which was filtered through Celite and evaporated to dryness under reduced pressure. The white residue was triturated with absolute ethanol and then dried at 0.2 torr and 50° for 24 hours to provide 3.0 g of the sodium phosphate title product as a white powder. The latter product characterized as follows, is the 2-chloro-2'-deoxyadenosine 5'-phosphate monosodium salt:

mp greater than 154° C. (dec.); $[\alpha]_D^{22}$ −34.3° (c 1.06, H$_2$O); H$^1$ NMR (DMSO) δ 8.50 (s, 1, H-8), 7.83 (s, 2, NH$_2$, D$_2$O exchangeable), 6.27 (t, J=7 Hz, peak width 14 Hz, 1, H-1'); IR (KBr) cm$^{-1}$ 1654, 1601, 1095, 1052; HPLC 100%;

Analysis calculated for C$_{10}$H$_{12}$ClN$_5$O$_6$PNa.1.0-H$_2$O.0.25 EtOH: C, 30.23; H, 3.75; N, 16.79; Cl, 8.50; H$_2$O, 4.32; Na, 5.51; P, 7.43. Found: C, 30.45; H, 3.60; N., 16.73; Cl, 8.92; H$_2$O, 3.52; Na, 5.50; P, 7.03 (0.25 EtOH determined by H$^1$ NMR).

(b) To obtain the disodium salt by the above procedure, an aqueous solution obtained after the ether extraction and removal of unwanted salts is passed through a column containing ion exchange resin material (e.g., Dowex 50) in the acid form, the resulting solution containing 2-chloro-2'deoxyadenosine 5'-phosphate free acid is treated with two equivalents of NaHCO$_3$ in aqueous solution, and the disodium salt is isolated by lyophilization of the reaction mixture.

EXAMPLES 2(a) TO 2(i)

The product as free acid or as a salt form other than the monosodium or disodium salt is obtained by passage of an aqueous solution of either the monosodium salt or the disodium salt through an ion-exchange column containing ion-exchange material (e.g. Dowex 50) in the acid form or the other form desired, exemplified by the following preferred embodiments.

| Form of Ion-Exchange Material | 2-Chloro-2'-deoxyadenosine 5'-Phosphate Compound |
| --- | --- |
| Acid Form | Free Acid |
| Potassium Form | Dipotassium Salt |
| Ammonium Form | Diammonium Salt |
| Lithium Form | Calcium Salt |
| Magnesium Form | Magnesium Salt |
| Barium Form | Barium Salt |
| n-Butylamine Form | Di-n-butylamine Salt |
| n-Octylamine Form | Di-n-octylamine Salt |
| Triethylamine Form | Di-triethylamine Salt |

PHARMACEUTICAL COMPOSITIONS

The following representative Examples 3 through 7, are given as illustrative pharmaceutical compositions utilizing different carriers. In these examples, Example 3 illustrates the use of the compounds of the invention in injectables suitable for intravenous injection. Example 4 describes an oral syrup preparation, Example 5 an oral capsule preparation and Example 6, oral tablets. Example 7 is directed to use of the compounds of the invention in suitable suppositories. For Examples 3 through 7, the ingredients are listed followed by the methods of preparing the compositions.

EXAMPLE 3

INJECTABLES

2-Chloro-2'-deoxyadenosine 5'-phosphate disodium salt 125 mg–500 mg

Water for Injection USP q.s.

The salt compound is dissolved in the water and passed through a 0.22 micron filter. The filtered solution is added to ampoules or vials, sealed and sterilized.

EXAMPLE 4

250 mg Active ingredient/5 ml syrup

| | |
|---|---|
| 2-Chloro-2'-deoxyadenosine 5'phosphate dipotassium salt | 25 g |
| Purified Water USP | 200 ml |
| Cherry Syrup q.s. or | 1000 ml |

The salt compound is dissolved in the water and to this solution the syrup is added with mild stirring.

EXAMPLE 5

CAPSULES 50 mg, 125 mg or 250 mg

| | |
|---|---|
| 2-Chloro-2'-deoxyadenosine 5'phosphate di-n-butylamine salt | 500 g |
| Lactose USP. Anhydrous q.s. or | 200 g |
| Sterotex Powder HM | 5 g |

Combine the salt and the lactose in a twin-shell blender equipped with an intensifier bar. Tumble blend for two minutes, blend for one minute with the intensifier bar and then tumble blend again for one minute. A portion of the blend is then mixed with the Sterotex Powder, passed through a #30 screen and added back to the remainder of the blend. The mixed ingredients are then blended for one minute, blended with the intensifier bar for thirty seconds and tumble blended for an additional minute. Appropriate sized capsules are filled with 141 mg, 352.5 mg or 705 mg of the blend, respectively, for the 50 mg., 125 mg and 250 mg containing capsules.

EXAMPLE 6

TABLETS 50 mg, 100 mg or 250 mg

| | |
|---|---|
| 2-Chloro'2'-deoxyadenosine 5'-phosphate di-triethylamine salt | 250 g |
| Corn Starch NF | 200.0 g |
| Cellulose, Microcrystalline | 46.0 g |
| Sterotex Powder HM | 4.0 g |
| Purified Water q.s. or | 300.0 ml |

Combine the corn starch, the cellulose and the salt compound together in a planetary mixer and mix for two minutes. Add the water to this combination and mix for one minute. The resulting mix is spread on trays and dried until a moisture level of 1 to 2 percent is obtained. The dried mix is then milled with a Fitzmill through a #RH2B screen at medium speed. The Sterotex Powder is added to a portion of the mix and passed through a #30 screen, and added back to the milled mixture and the total blended for five minutes by drum rolling. Compressed tablets of 150 mg, 300 mg and 750 mg respectively, of the total mix are formed with appropriate sized punches for the 50 mg, 100 mg or 250 mg containing tablets.

EXAMPLE 7

SUPPOSITORIES 125 mg, 250 mg or 500 mg per 3 g

| | | | |
|---|---|---|---|
| 2-Chloro-2'-deoxyadenosine 5'-phosphate di-n-octylamine salt | 125 mg | 250 mg | 500 mg |
| 1540 Polyethylene Glycol | 1925 mg | 1750 mg | 1400 mg |
| 8000 Polyethylene Glycol | 825 mg | 750 mg | 600 mg |

Melt the Polyethylene Glycol 1540 and the Polyethylene Glycol 8000 together at 60° C. and dissolve the salt compound into the melt. Mold this total at 25° C. into appropriate suppositories.

Having described the invention, the embodiments of the invention in which an exclusive property or privilege is claimed are defined as follows:

1. A method for treating microbial infection which comprises administering an antimicrobially effective amount of a 2-chloro-2'-deoxyadenosine 5'-phosphate compound in pharmaceutically acceptable dosage form to an animal in need thereof, said compound having the structural formula:

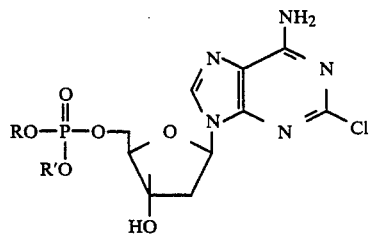

where R and R' each independently represent H, NH$_4$, an alkali metal or a C$_1$ to C$_8$ alkylamine or together represent an alkaline earth metal.

2. A method for treating viral infection of a virus selected from cytomegalo virus, herpes simplex virus, and vaccinia virus, which comprises administering an effective virus growth inhibiting amount of a 2-chloro-2'-deoxyadenosine 5'-phosphate compound in pharmaceutically acceptable dosage form to an animal in need thereof, said compound having the structural formula:

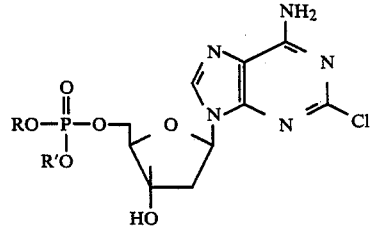

where R and R' each independently represent H, NH$_4$, an alkali metal or a C$_1$ to C$_8$ alkylamine or together represent an alkaline earth metal.

* * * * *